United States Patent
Wu

(10) Patent No.: US 10,179,149 B2
(45) Date of Patent: *Jan. 15, 2019

(54) METHODS AND SYSTEMS FOR PROCESSING EXOSOMES

(71) Applicant: Allan Yang Wu, Cathedral City, CA (US)

(72) Inventor: Allan Yang Wu, Cathedral City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/280,399

(22) Filed: Sep. 29, 2016

(65) Prior Publication Data

US 2017/0049817 A1 Feb. 23, 2017

Related U.S. Application Data

(63) Continuation of application No. 14/079,243, filed on Nov. 13, 2013, now Pat. No. 9,480,714.

(60) Provisional application No. 61/796,540, filed on Nov. 13, 2012.

(51) Int. Cl.
| | | |
|---|---|---|
| *A61K 35/14* | (2015.01) | |
| *B03C 1/01* | (2006.01) | |
| *B03C 1/28* | (2006.01) | |
| *B03C 5/00* | (2006.01) | |
| *B03C 5/02* | (2006.01) | |

(52) U.S. Cl.
CPC ............... *A61K 35/14* (2013.01); *B03C 1/01* (2013.01); *B03C 1/288* (2013.01); *B03C 5/005* (2013.01); *B03C 5/026* (2013.01); *B03C 2201/18* (2013.01); *B03C 2201/26* (2013.01)

(58) Field of Classification Search
CPC ..................................................... A61K 35/14
See application file for complete search history.

(56) References Cited

U.S. PATENT DOCUMENTS

| | | |
|---|---|---|
| 7,897,356 B2 | 3/2011 | Klass et al. |
| 9,480,714 B2 | 11/2016 | Wu |
| 2009/0220944 A1 | 9/2009 | Fais |
| 2009/0258379 A1 | 10/2009 | Klein et al. |
| 2012/0070858 A1 | 3/2012 | Contreras et al. |

FOREIGN PATENT DOCUMENTS

| | | | |
|---|---|---|---|
| WO | 2010141862 A2 | 12/2010 | |
| WO | 2011063324 A2 | 5/2011 | |
| WO | WO-2012053976 A1 * | 4/2012 | ............... A61K 8/14 |

OTHER PUBLICATIONS

PCT/US2013/069901 International Search Report and Written Opinion dated Feb. 12, 2014.
Chen et al. "Microfluidic isolation and transcriptome analysis of serum microvesicles." Lab Chip, Feb. 21, 2010, 10(4):505-511, NIH.
Pawlowski et al. "Abstract 3018: Identifying and characterizing subpopulation of exosomes to provide the foundation for a novel exosoome-based cancer diagnostic platform." Cancer Research, Apr. 15, 2010, 70(8) Supplement 1.
Clayton et al. "Analysis of antigen presenting cell derived exosomes, based on immuno-magnetic isolation and flow cytometry." J of Immunological Methods, 2001, 247:163-174.

* cited by examiner

*Primary Examiner* — Bin Shen
(74) *Attorney, Agent, or Firm* — Wagenknecht IP Law Group PC

(57) ABSTRACT

Methods and systems of processing exosomes from a biologic sample, including providing a biological sample having a mixed population of exosomes, wherein the mixed population of exosomes includes two or more distinct subpopulations of exosomes; processing the biological sample to selectively remove one or more exosome subpopulations from the mixed population of exosomes thereby obtaining a sample enriched with a desired subpopulation of exosomes; and adding the enriched sample of exosomes to a pharmaceutically acceptable carrier.

9 Claims, 13 Drawing Sheets

METHODS AND SYSTEMS FOR PROCESSING EXOSOMES

CROSS REFERENCE TO RELATED APPLICATIONS

This is a continuation of U.S. patent application Ser. No. 14/079,243, filed Nov. 13, 2013, now U.S. Pat. No. 9,480,714, which claims benefit of priority to U.S. provisional patent application Ser. No. 61/796,540 filed Nov. 13, 2012.

TECHNICAL FIELD

The invention relates generally to methods and systems for the isolation or purification of components from biological samples and more specifically, to a method of processing exosomes to selectively remove one or more exosome subpopulations from a mixed population of exosomes thereby obtaining a sample enriched with a desired subpopulation of exosomes.

BACKGROUND OF THE INVENTION

Exosomes are small 50 to 90 nm membrane vesicles containing nucleic acids and protein. They may be found naturally occurring in numerous biologic fluids such as blood and urine and a secreted by a number of different cell types. The genetic information within the exosome may easily be transmitted by fusing to the membranes of recipient cells, and releasing the genetic information into the cell intracellularly. Some patents have articulated upon the use of exosomes for therapeutic purposes. Patent application Ser. No. 12/298,467 generically uses filtration of biologic fluids to isolate exosomes for therapy. U.S. Pat. No. 6,899,863 uses exosomes that have been gel purified from supernatants from cell culture. Patent application 20090304677 uses a filtration device to remove all exosomes from human plasma and thereby removing carcinogen associated exosomes in an ex-vivo dialysis fashion.

Though exosomes as a general class of compounds represent great therapeutic potential, the general population of exosomes are a combination of several class of nucleic acids and proteins which have a constellation of biologic effects both advantageous and deleterious. In fact, there are over 1000 different types of exosomes. Of particular interest are the proteins and nucleic acids which induce apoptosis and oxidation. These particular functional groups are not universally conducive to therapy related to skin rejuvenation or cosmetic aesthetic applications, though some exosomal oxidation enhancing proteins and nucleic acids could be of use in circumstances of skin infections and some forms of acne. Additionally exosomes related to apoptosis can be used to induce fat cell death in unwanted locations such as excess fat of the abdomen, buttock, eye bags and jowls. The best practice for exosome therapy therefore, would involve removal of unwanted components or subpopulations or isolating specific subpopulations for therapy. At present, there are no patents, patent applications or scientific literature which incorporates this novel approach. Part of the reason for this gap is related to the limitations of standard sorting technologies like flow activated sorting, which is limited by the sheer number of flourochromes that may be used and the considerable expense of equipment. More cost effective magnetic separation may be an alternative method for high number multiplex sorting, however, high number magnetically active antibodies and oligonucleotides can create reagent clumping and off target binding. Hence, a cost and time efficient method sorting desired and undesired components of exosomes, both protein and nucleic acid based, would present great utility and therapeutic potential.

SUMMARY OF THE INVENTION

The present invention provides a methods and systems for the processing of exosomes that address the above challenges and thus provide related benefits. In one aspect of the invention a method of processing exosomes from a biologic sample is provided, including providing a biological sample having a mixed population of exosomes, wherein the mixed population of exosomes includes two or more subpopulations of exosomes having a different subpopulation characteristic; and processing the biological sample to selectively remove one or more exosome subpopulations from the mixed population of exosomes thereby obtaining a sample enriched with a desired subpopulation of exosomes. The methods and systems may be used with any biological sample having or suspected of having a mixed population of exosomes, such as blood, urine, serum, saliva, sputum, a bronchio alveolar lavage, a liposuction aspirate fluid, a liposuction fluid waste, peritoneal dialysis sample, and a tissue culture supernatant.

In some embodiments, the desired subpopulation of exosomes is among the one or more exosome subpopulations selectively removed from the mixed population; however, in other embodiments one or more exosome subpopulations are removed from the mixed population thereby leaving the desired subpopulation of exosomes and thus providing a negative selection approach. Selectively removing the one or more exosome subpopulations can include selectively capturing exosomes from the mixed population and permitting passage of remaining exosomes.

Selectively capturing exosomes can include capturing the exosomes to binding agents, such as antibodies or antibody fragments that are fixed to a substrate. In another approach, selectively capturing exosomes can include exposing the mixed population to binding agents that selectively bind the one or more exosome subpopulations and capturing the binding agents and thus bound exosomes. To this end, binding agents can be labeled with magnetic particles or particles that are magnetizable and capture of such binding agents can be accomplished by exposing the particles to a suitable magnetic field or a suitable electric field. Further, the binding agents can be labeled with particles that permit selective capture and optionally selective release by modulation of the magnetic field, an electric field or temperature. In still further embodiments, the magnetic field or electrical field is selectively activated in response to a signal generated from the presence of exosomes. Such a signal can itself be a detectable change in an electric field or a change in optical property, such as by detecting fluctuations in electric field by the presence of exosomes, optionally bound to binding agents, or by binding agents coupled to optically detectable beads, thereby triggering activation.

In some embodiments, the binding agent traverses the exosome membrane to bind a biomarker encapsulated within the exosome. Such methods may include a step to permeate the exosome membrane to accept the binding agent.

In some embodiments it is desirable to collect the captured exosome or the exosome's biomarker. In one such technical approach, a binding agent may be labeled with a magnetic particle, the binding agent may be permitted to bind the biomarker of the exosome, magnetic attraction can be utilized to capture the exosome, then the biomarker may be selectively released from the binding agent while maintaining capture of the binding agent thereby permitting collection of the previously captured exosome. In another such technical approach, a binding agent may be labeled with a magnetic particle, the binding agent may be permitted to bind the biomarker of the exosome, magnetic attraction can be utilized to capture the exosome through attraction with the binding agent, the binding agent-biomarker pair can then be de-nuded of the surrounding exosome components, then the binding agent-biomarker pair may be released from the binding agent. In still another technical approach, a binding agent may be labeled with a magnetic particle, the binding agent may be permitted to bind the biomarker of the exosome, magnetic attraction can be utilized to capture the exosome through attraction with the binding agent, the binding agent-biomarker pair can then be de-nuded of the surrounding exosome components, then the biomarker may be released from the binding agent, such as by modulation of temperature while maintaining magnetic attraction with the binding agent, and optionally re-incapsulating the biomarker in a capsule for collection.

In other embodiments, the binding agents are labeled with an optical marker and the step of capturing the binding agents is performed by optical detection coupled to a cell sorting apparatus, such as those used in fluorescent activated cell sorting (FACS). In still other embodiments, the binding agents are labeled with oligonucleotides, optionally where binding agents for different exosome populations are labeled with different oligonucleotides to permit selective capture to complementary oligonucleotides and optionally selective release from the complementary oligonucleotides. Such selective capture and optional selective release can be regulated by modulation of temperature.

In some embodiments, the invention provides methods of processing the biological sample, which include providing a system comprising a microfluidic device, the microfluidic device including a capture chamber having an entry passage and exit passage that are fluidicly coupled, the capture chamber having binding agents that selectively bind subpopulations of exosomes and the capture chamber configured to selectively prevent bound exosomes from exiting the exit passage; providing the mixed exosome population in a liquid medium; and inducing flow of the mixed exosome population through the microfluidic device to capture exosomes bound to the binding agents. In some embodiments, the binding agents are immobilized to a substrate.

The system may also include a device station with a power source. In such systems, the capture chamber can include a dielectrophoretic element operably connected to the power source, where powering the dielectrophoretic element induces a mixing of the mixed exosome population with binding agents within the capture chamber and/or preventing or diverting the flow of bound exosomes away from the exit passage, such as being provided as a blocking electrode. In another approach the binding agents are labeled with particles capable of capture by a magnetic field and the capture chamber includes a substrate having an electromagnetic element operably connected to the power source, where powering the electromagnetic element results magnetic attraction between the substrate and the particles thereby preventing flow of bound exosomes from the exit passage of the chamber. In still another approach the agents are labeled with oligonucleotides and the capture chamber includes a substrate having complementary bound oligonucleotides and that is operably connected to the power source, where powering the substrate such as through a heating element results in an increase in temperature thereby permitting release of oligonucleotides from complementary nucleotides.

In a related approach, a step of processing the biological sample is performed by providing a system including a microfluidic device having a labeling chamber fluidicly joined and upstream to a capture chamber, where the labeling chamber includes binding agents that selectively bind subpopulations of exosomes and the capture chamber being configured to capture exosomes bound to the binding agents and to permit unbound exosomes to pass outward from an exit passage of the capture chamber or device; providing the mixed exosome population in a liquid medium; and inducing flow of the mixed exosome population through the microfluidic device to capture exosomes bound to the binding agents. In such systems, the capture chamber can be provided with capture molecules, such as immobilized capture molecules, that themselves selectively capture the binding agents. Captured exosomes can be selectively released through electronic communication with the structure used for capture.

This related system can also include a device station having a power source. In some embodiments, at least one dielectrophoretic element is operably connected to the power source, where powering the dielectrophoretic element results in at least one function selected from the group consisting of inducing a mixing of mixed exosome population and binding agents, such as within the labeling chamber, and preventing or diverting the flow of bound exosomes away from the exit passage. Alternatively, the binding agents are labeled with particles capable of capture by a magnetic field and the capture chamber includes a substrate having an electromagnetic element operably connected to the power source, wherein powering the electromagnetic element results magnetic attraction between the substrate and the particles thereby preventing flow of bound exosomes from the exit passage. In another embodiment, the binding agents are labeled with oligonucleotides and the capture chamber includes a substrate having complementary bound oligonucleotides and operably connected to the power source, where powering the substrate results in an increase in temperature thereby regulating capture or release of oligonucleotides from complementary nucleotides.

Desired subpopulations of exosomes can be further processed by their combination with a pharmaceutically acceptable carrier to form a pharmaceutical. Similarly, desired subpopulations of exosomes can be combined with a cosmetically suitable carrier to form cosmetics. Thus, the invention also provides a method of introducing one or more desired exosome subpopulations to a subject, which includes processing a subpopulation from a biological sample, forming a pharmaceutical and introducing the pharmaceutical to the subject. Similarly, the invention also provides a method of introducing one or more desired exosome subpopulation to a subject, which includes processing a subpopulation of exosomes from a biologic sample, forming a cosmetic and introducing the cosmetic to the subject.

In another aspect of the invention, the invention provides a system for processing an exosome subpopulation from a biological sample having a mixed population of exosomes, the system including a microfluidic device, the microfluidic device itself including a capture chamber having an entry passage and exit passage that are fluidicly coupled, the capture chamber having binding agents that selectively bind subpopulations of exosomes and the capture chamber configured to selectively prevent bound exosomes from exiting the exit passage. In some embodiments, the binding agents are immobilized to a substrate.

In a related aspect, the invention provides a system for processing an exosome subpopulation from a biological sample having a mixed population of exosomes, the system including a microfluidic device having a labeling chamber fluidicly joined and upstream to a capture chamber, wherein the labeling chamber has binding agents that selectively bind subpopulations of exosomes and the capture chamber being configured to capture exosomes bound to the binding agents and to permit unbound exosomes to pass outward from an exit passage. The microfluidic device may also regulate or modulate the selective release of captured exosome subpopulations.

BRIEF DESCRIPTION OF THE DRAWINGS

FIG. 3A depicts magnetic capture of an antibody 18 bound to a surface biomarker 22 of an exosome 24. Magnetic and dielectrophoretic features are regulated by a power station 24. FIG. 3B depicts magnetic capture of an antibody 18 bound to a biomarker 22 encapsulated in the exosomes. In both FIGS. 3A and 3B, different sized magnetic particles 28a, 28b are shown to demonstrate variable magnetic attraction with a same magnetic element for selective release by the power station 26.

FIG. 4 shows an approach to capturing exosomes 24 using nucleic acids 30. Temperature of the substrate is modulated by the power station 26 through a heating element 32 to permit annealing and melting of nucleic acid labels 30a.

In FIG. 6A, a sample of mixed exosomes 24, 36 is mixed with binding agents 38 to bind surface biomarkers 22 from subpopulations of exosomes 24. FIG. 6B demonstrates the selective capture of bound exosomes 24. FIG. 6C depicts the outward flow of the unbound exosomes 36 to form an enriched population of desired exosomes.

In FIG. 7A, a sample of mixed exosomes 24, 36 is mixed with binding agents 38 to bind surface biomarkers 22 on undesired exosomes 24. FIG. 7B demonstrates the selective capture of bound exosomes 24 by the activation of a magnetic substrate 20, which itself is activated by passage of bound exosomes across a detector 40. FIG. 7C depicts the outward flow of the unbound exosomes 36 to form an enriched population of desired exosomes. FIG. 7D depicts the turning off of the magnetic substrate 20 to permit passage of bound exosomes 24 the exit aperture.

In FIG. 8A, a sample of mixed exosomes 24, 36 is mixed with binding agents 38 to bind biomarkers encapsulated within undesired exosomes. FIG. 8B demonstrates the selective blocking of bound exosomes 24 by the activation of a blocking electrode 34, which itself activated by passage of bound exosomes 24 across the detector 40. FIG. 8C depicts the outward flow of the unbound exosomes 36 to form an enriched population of desired exosomes. FIG. 8D depicts the turning off of the blocking electrode 34 to permit passage of bound exosomes 24.

DETAILED DESCRIPTION OF PREFERRED EMBODIMENTS

Figure 1:
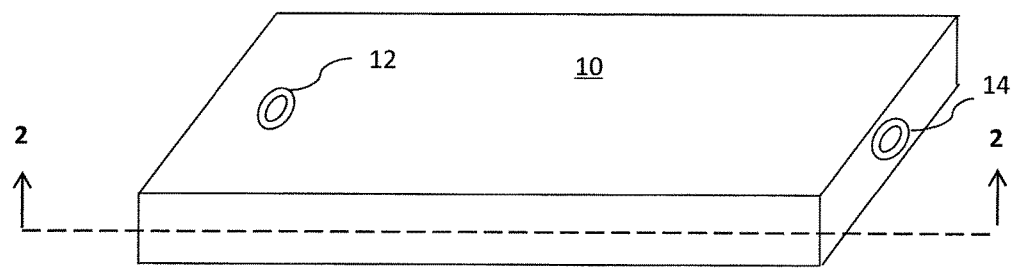
FIG. 1 is an illustration showing a microfluidic device formed as a single capture chamber with entry 12 and exit 14 apertures.

The primary object of the invention is provide methods and systems for the processing of a mixed population of exosomes, such as from a biological sample, to enrich for a desired subpopulation of exosomes and the use of the desired subpopulation of exosomes in the preparation of a pharmaceutical or cosmetic formulation. Other objects will be provided in view of the various features discussed herein. As an introduction, the following provides a general definition of commonly used terms.

The term "biological sample" as used herein refers to a specimen at least partly obtained from a subject, preferably a human. A "biological sample" also encompasses a population of cultured exosomes after their harvest from a subject. The biological sample may be liquid or may be a solid that is capable of suspension in a liquid to facilitate flow through a fluid chamber or device used for enrichment.

The term "mixed population of exosomes" as used herein refers to a population of exosomes that has two or more subpopulations, each having a distinct characteristic. A "mixed population of exosomes" may be a population of exosomes obtained from a total exosome purification protocol starting with a harvested biological sample or may be collected from culture conditions. The term "subpopulation of exosomes" as used herein refers to a group of exosomes that share a characteristic that is not shared by all exosomes in the mixed population. The term "desired subpopulation of exosomes" as used herein refers to one or more subpopulations of exosomes that are the object of the processing procedure for enrichment. The term "enriched" as used herein refers to an increase in relative abundance compared to a relative abundance prior to the "enrichment."

The term "fixed to a substrate" as used herein refers to the immobilization of a moiety, such as antibody or antibody fragment to a substrate thereby preventing its release under normal operating conditions.

The term "antibody fragment" as used herein refers to a Fc, F(ab), F(ab')2 of an immunoglobulin. An "antibody fragment" may be a heavy chain, light chain or a combination of both.

The term "binding agent" as used herein refers to a molecule that has a binding affinity to biomarker. A "binding agent" is used in the capture of an exosome through binding to its biomarker.

The term "biomarker" as used herein refers to a moiety that forms part of an exosome or that is encapsulated within an exosome. A "biomarker" includes a region that permits binding to a binding agent. Examples of biomarkers are membrane proteins, proteins encapsulated within an exosome or nucleic acids encapsulated in an exosome.

The term "permitted to bind" as used herein refers to a binding agent and its corresponding biomarker being exposed to one another under conditions that would allow their binding. Such conditions may include permeating the exosome membrane to permit entry of the binding agent and/or regulating a temperature such that complementary nucleic acid sequences can anneal.

The term "de-nuding" or "de-nuded" as used herein refers to the removal of the exosome membrane and encapsulated components from the binding agent or from the binding agent-biomarker pair. De-nuding can be performed by exposing the exosome to a chemical, a suitable electric field and/or under suitable pressure.

The term "dielectrophoretic element" as used herein refers to an electrode with appropriate circuitry attached to a power source that is capable of dielectrophoresis.

The term "blocking electrode" as used herein refers to an electrode capable of emitting an electrical signal that prevents a label from traversing the electrode. A "blocking electrode" can be used to prevent release of a subpopulation of labeled exosomes through an exit aperture of a microfluidic capture chamber and may operate consistent with delectrophoretic principles.

The term "oligonucleotide" as used herein refers to a nucleic acid sequence from about 4-30 nucleic acid sequences.

Methods for Processing Exosomes

While the object of the invention is to provide methods that result in the enrichment of a subpopulation of exosomes, whether natural or synthetic, the steps of processing the mixed population of exosomes and subsequently enriched subpopulations of exosomes can vary depending on technical approach or desired outcome.

In one aspect of the invention a method of processing a subpopulation of exosomes from a biologic sample is provided, including providing a biological sample having a mixed population of exosomes, wherein the mixed population of exosomes includes two or more subpopulations of exosomes having a different subpopulation characteristic; and processing the biological sample to selectively remove one or more exosome subpopulations from the mixed population of exosomes thereby obtaining a sample enriched with a desired subpopulation of exosomes.

The methods and systems may be used with any biological sample having or suspected of having a mixed population of exosomes, such as blood, urine, serum, saliva, sputum, a bronchio alveolar lavage, a liposuction aspirate fluid, a liposuction fluid waste, peritoneal dialysis sample, and a tissue culture supernatant. Biological samples may be collected or harvested from subjects using any suitable techniques according to the particular sample collected. Among these can include drawing blood, scraping or digesting tissue, collecting aspirates or the like. Depending on the particular sample, the sample may require further processing to obtain a mixed population of exosomes prior to selective enrichment steps. A variety of laboratory protocols are available to those skilled in the art as well as a variety of commercially available products for harvesting total exosomes from biological samples.

As a non-limiting example, a collected blood sample may be centrifuged to separate the sample into a serum layer and cellular pellet of blood cells. The serum can then be processed to purify total intact exosomes from the serum such as those offered by Life Technologies (Carlsbad, Calif.). Alternatively, total exosomes may be obtained using a differential ultracentrifuation approach where a biological sample is repeatedly centrifuged at increasing speeds with the pellet being repeatedly discarded until ultimately the pellet contains the exosomes from the sample thereby forming a suitable population of total exosomes for enrichment of a subpopulation. In still other methods, centrifugation followed by size filtration through suitable pore size permits collecting total exosomes from biological samples.

Once the mixed population of total exosomes is purified by the removal of tissue, cells, cellular debris and the like, the processing method to selectively remove one or more exosome subpopulations may proceed or alternatively, the total or mixed exosome population may be cultured. If culturing exosomes, it is advisable to consider whether contaminating exosomes may be present in the intended culture medium and thus it may be preferred to use a basal culture medium with nutrients but without fetal bovine serum (FBS) or alternatively substituting bovine serum albumin (BSA) for FBS may be acceptable. Methods for culturing exosomes may be found in the biological arts and thus are incorporated herein by reference.

Whether the mixed exosomes are collected directly from a biological sample or whether a total exosome population is obtained from culture, a desired subpopulation of the mixed exosome population is selectively enriched by selective removal of one or more other subpopulations. Subpopulations can be selected based on characteristics that are indicative, at least in part, of the particular subpopulation or shared among fewer than all exosomes.

In furtherance of the above, subpopulations can be characterized and thus designated to one or more subpopulations using a variety of approaches. In some instances, subpopulations are characterized according to the presence or absence of a surface moiety displayed on the surface of the exosome. In another embodiment, the subpopulations are characterized according to the presence or absence of one or more RNA molecules, such as mRNA or miRNA, encapsulated within the exosome. In still other embodiments, exosomes are characterized by the presence or absence of one or more polypeptide sequences or proteins encapsulated within the exosome. In still other embodiments, exosomes are characterized according to exosome target, such as lymphocyte targeting exosomes. In still other embodiments, exosomes are characterized according to a medical condition, such as an exosome affected or released from a cancer cell.

Since the object of the invention is to enrich at least one exosome subpopulation compared to other exosome subpopulations, one skilled in the present art will understand that the degree of enrichment can vary. It is generally preferred to enrich a desired exosome population such it is at least 60%, more preferably 70%, more preferably 80%, more preferably 90%, more preferably 95%, more preferably 96%, more preferably 97%, more preferably 98%, more preferably 99%, and most preferably 100% of final exosome population. In some embodiments, the desired subpopulation of exosomes is among the one or more exosome subpopulations selectively removed from the mixed population; however, in other embodiments one or more exosome subpopulations are removed from the mixed population such that the desired subpopulation of exosomes remains. A desired subpopulation of exosomes may include those that have a mixture of desired biomarkers. In still other embodiments, multiple rounds of enrichment are performed, which may include two or more different enrichment approaches. In still another approach, the enriched exosome population is an artificial exosome population formed by the re-encapsulation of one or more different biomarkers that had been previously de-nuded from surrounding exosomes.

As nonlimiting examples, exosomes that are typically undesired for further processing to ultimately form a pharmaceutical or cosmetic formulation include those that are obtained from cancer cells. In addition exosomes belonging to a subpopulation associated with oxidation, apoptosis and the like are generally undesired for incorporation into a pharmaceutical or therapeutic formulation but my be desired for research purposes. To this end, processing of exosomes for pharmaceutical or cosmetic use may include the selective removal of exosomes that may result in increased oxidation, apoptosis or the like; however, such populations may be further processed for other purposes and thus selectively released for separate collection.

As already eluded to, selection of one or more exosome subpopulation is based on selection according to one or more biomarkers, which can be present on the surface of the exosome, may be associated with the outer exosome membrane or may be encapsulated within the exosome. The invention envisions that biomarkers whether naturally occurring or engineered will continue to be identified or developed and thus the technical approach is non-limiting to any particular polypeptide, nucleic acid or organic compound so long as a suitable binding agent can be configured to bind and thus label the biomarker for its targeting. The skilled artisan will appreciate that selection for a desired subpopulation may be accomplished by binding the desired subpopulation or alternatively binding the majority of all other subpopulations such that the absence of binding results in an enriched subpopulation.

In some embodiments the biomarker is polypeptide that is exposed on the outer exosome membrane surface. Targeting such surface markers can be a favorable approach as it permits selection to based at least in part on surface characteristics which may be biologically relevant for cells targeted by the exosome as well as conveniently displaying an exposed surface moiety for a binding agent, such as a polyclonal or monoclonal antibody or antibody fragment (F(ab) or F(ab')2) to access.

In some embodiments, the biomarker is a nucleic acid sequence, such as an RNA sequence, a messenger RNA (mRNA) sequence, or a microRNA (miRNA) sequence. RNA provides a favorable biomarker for selection because of its biological importance in the translation and regulation of translation to protein, as well as its ability to bind complementary single strand nucleic acid sequences, such as synthetic oligonucleotides. When targeting RNA for selection by a binding agent, such as a labeled oligonucleotide, the oligonucleotide must traverse the outer exosome membrane and thus can be coupled with methods to permeate or temporarily disrupt the exosome membrane. Such approaches may include chemical treatment, such as with a suitable detergent, or electroporation where a charge temporarily permeates the membrane to permit uptake of the charged nucleic acid sequence. In some approaches the binding agent maybe encapsulated or masked by the presence of lipids for delivery. The skilled artisan will appreciate that binding an oligonucleotide to a nucleic acid sequence is accomplished through the matching of the genetic code, namely matching bases of guanine (G) to cytosine (C) and adenine (A) to thymidine (T). Further, greater lengths of complementary nucleic acid bases generally provide stronger and more specific bonding as opposed shorter lengths or mismatched bases. The skilled artisan will appreciate that given the nucleic acid sequence of interest, synthetic oligonucleotides can be designed to various regions and with various specificities. Generally, nucleic acid spans of about 10-50 nucleotides can be targeted, 15-25 nucleotides, 10-20 nucleotides or the like as appropriate for the nucleic acid sequence. The skilled artisan will appreciate that short spans will be generally preferred when targeting microRNAs as they are typically about 19-25 nucleotides in length. The entire or less than entire span of microRNA may be targeted. This length is also convenient as the melting temperature of bound oligonucleotides can vary permitting the selective release of captured subpopulations by modulating the surrounding temperature. In a related approach the binding agent is a polypeptide sequence, protein, antibody or the like capable of binding to the RNA and labeled with a selectable label, such as a magnetic particle, fluorescent molecule or the like. Binding agents that are not commercially or readily available may be generated, such as by oliognucleotide synthesis or antibody creation in response to exposure to antigen as known in the art.

In other embodiments, the biomarker is a polypeptide or protein. Targeting polypeptide sequences or protein provides a favorable marker for selection due to the biological importance of protein as well as the ability to generate polyclonal or monoclonal antibodies or antibody fragments for specific binding to polypeptides or protein. Further, antibody technology facilitates the attachment to a variety of labels, which can be used for capture. When targeting polypeptide or protein housed within the exosome, typically methods for permeating or disrupting the exosome are utilized.

When considering whether a biomarker is desired or undesired biomarkers, such as various miRNAs, the skilled artisan will appreciate that desirability or undesirability can differ depending on medical condition or stage of treatment and the like. Accordingly, while reference to particular biomarkers is provided, each should be considered in context to the desired treatment.

In view of the above, the following is a non-limiting listing of miRNAs that may be of particular interest as being generally desired given different conditions: 21 may be beneficial for heart ischemia reperfusion, 669a may be for helping congestive heart failure, 24 may be beneficial for angiogenesis, 23b may be beneficial for suppression of bladder cancer, 196a may be beneficial for mitigating Huntington symptoms, the 200 family may be beneficial for forming induced pluripotent stem cells, and Let-7 exhibits antitumor properties.

While non-limiting the following may warrant consideration for removal from a mixed population of miRNAs: 22 and 499 may be less beneficial for heart conditions as it may cause or lead to myopathy/hypertrophy, 106b may cause or lead to mitochondrial dysregulation, 149 may cause or lead to osteoarthritis, 296 may cause or lead to tumor angiogenesis, Her2 surface protein of exosome may cause or lead to breast cancer.

In furtherance of the above, the skilled artisan can consider biomarkers in view of the following considerations. In the case of breast and breast cancer miRNAs: 495, 181, 146a and 196b are upregulated. In the case of lung cancer 150 is upregulated. In the case of immune activity and hypoxia associated with cancer 21, 125b, 155, 196, 210 are upregulated.

In the HeLa (cervical cancer) cell line, inhibition of the following miRNAs leads to decreased cell growth: 95, 124, 125, 133, 134, 144, 150, 152, 187, 190, 191, 192, 193, 204, 211, 218, 220, 296, 299, however, inhibition of these leads to increased cell growth: 21 and 24. Further, in HeLa the following cause apoptosis 7, 148, 204, 210, 216, and 296.

While the above biomarkers might be generally be considered more or less desirable, the following miRNAs tend to have mixed effects (possibly deleterious and beneficial) depending on a disease state and thus should be considered in regards to the particular condition by the skilled artisan: 122 and 155.

While enriching desired subpopulations may be desired to form pharmaceuticals or cosmetics themselves, miRNAs can regulate stem cell differentiation too and can be used in conditioned media to create different cellular therapies ex-vivo and even potentially in-vivo. To this end, the following is non-limiting listing of additional miRNAs that warrant consideration by the skilled artisan: 9, 26b, 34a, 124, 125b, and Let-7 develops neurons; 184 inhibits development of neurons; 27, 29a/b, 335, 155, 223, 23b, 140, 675 develops chondrocytes and osteocytes; 18a, 145, 199a, 221 inhibits development of chondros and osteos; 1, 204, 499 develops cardiomyocytes; 124 inhibits development of cardiomyocytes; 1, 10a, 145 develops smooth muscle cells; 181a develops endothelial cells; 7641 inhibits development of endothelial cells; 17-92 cluster maintains stem cell pluripotency; 21, 29a/b, 106a-363, 200c may be helpful in reprogramming somatic cells into stem cells; 34 and Let7 family inhibits reprogramming of somatic into stem cells.

In one approach, processing the biological sample or cultured sample includes selectively removing one or more exosome subpopulations by selectively capturing exosomes from the mixed population and permitting passage of remaining exosomes. In such embodiments the remaining exosomes can be collected as the desired subpopulation. Enriching for a desired subpopulation can be accomplished using a variety approaches, among these include the use of a magnetic field in the case of magnetic and paramagnetic antibodies and/or oligonucleotides, a dielectrictrophoretic field, a eletrophoretic field, an electrical field, two charged plates, direct current, alternating current, light waves, ultrasound waves/energy, sinusoidal wave form electrical energy, non-sinusoidal wave form electrical energy, patterned interruption of electrical energy, and a flow activated cell sorter or lab-on-chip micro or nano device to separate by fluorescence or color in the case of flourochrome antibodies and/or oligonucleotides.

Figure 2:
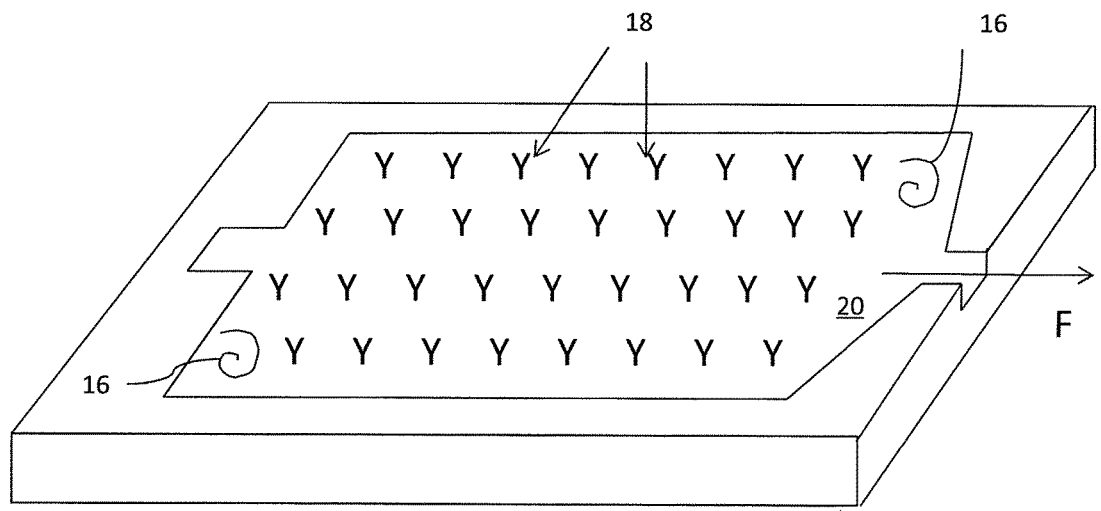
FIG. 2 is a cutaway view from FIG. 1 across 2-2, which depicts a flow path F through hollow interior of the capture chamber thereby exposing a sample to dielectrophoretic elements 16 and antibody 18 bound to the substrate 20.

Turning briefly to the drawings, an example of a microfluidic device is shown in FIG. 1 and its cross section shown in FIG. 2. Specifically, the above can be accomplished by providing a capture chamber having entry 12 and exit 14 apertures that are fluidicly coupled through a hollow interior thereby forming a flow direction F. Naturally one or more chambers may be provided in series or parallel in a microfluidic system and may be attached to tubing, reagent reservoirs or the like. By immobilizing or fixing a binding agent, such as in the form of antibodies 18, to a surface within the hollow interior, selective capture of exosomes can be accomplished thereby selectively depleting subpopulations of exosomes from the sample as it proceeds along the flow direction. A dielectrphoretic element 16 is also shown, which may assist with sample mixing and thus to permit binding between binding agent and biomarker or to encourage a directional flow of the sample.

Figure 3A:
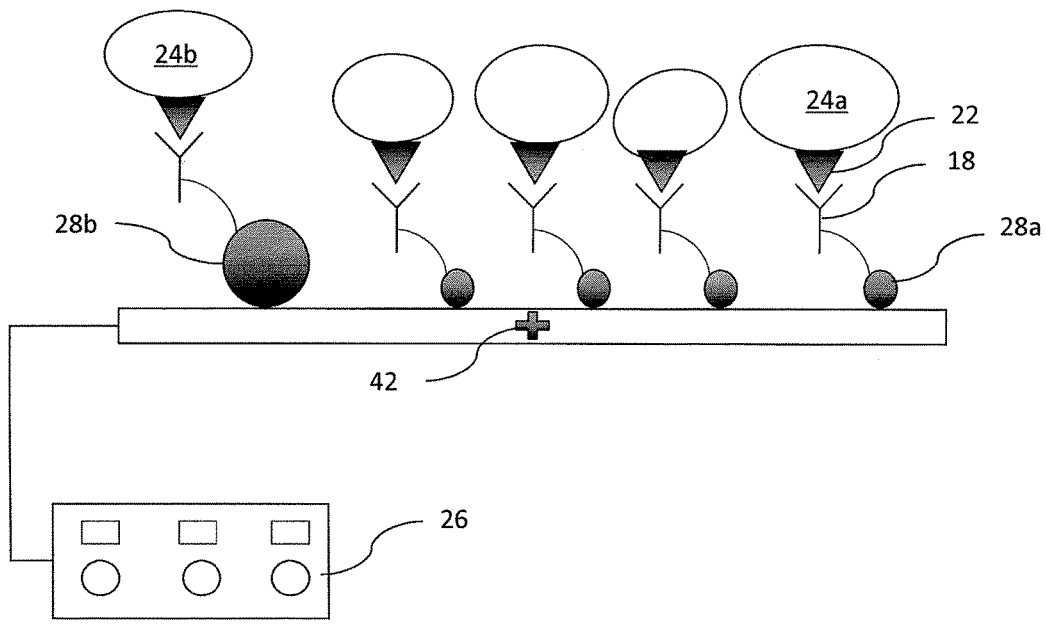
FIGS. 3A-B show approaches to capturing exosomes using magnetic capture.

In another variation, selectively capturing exosomes can include exposing the mixed population to binding agents that selectively bind the one or more exosome subpopulations, followed by capturing the binding agents and thus capturing exosomes. An example is shown in FIG. 3A where instead of permanently immobilizing the binding agent, magnetically labeled antibodies 18 are labeled with magnetic beads or a magnetizable metal referred to collectively herein as "magnetic particles" 28a, 28b, thereby permitting capture to an inducible magnetic substrate such as by activating an electromagnet 42. This configuration provides an added benefit in that magnetic attraction can be modulated by the use of different sized magnetic particles 28a, 28b, and thus labeling antibodies 18 specific to particular subpopulations 24a, 24b with different sized particles 28a, 28b can permit the user to sequentially release the captured exosomes 24 by modulating the current to the elecrtromagnet 42. Such modulation can be performed by the electrically connecting a base unit 26 with power source that can modulate the current to the electromagnetic substrate 20.

Thus, varying the current or polarity can vary the resulting resistance to external forces present in the chamber, such as from fluid flowing through the microfluidic device or against dielectrophoretic forces encouraging movement of the exosome. The skilled artisan will appreciate that magnetic attraction can also be modulated by labeling different subpopulations with labels formed from elements having different degrees of attraction to a same magnetic field thereby permitting the release of labels having weaker attraction before those with greater magnetic attraction. Release can be accomplished by increased fluid flow rate or by balancing the magnetic field with activation of a dielectrophoretic element, which again can be configured to push exosomes towards the exit aperture.

Figure 3B:
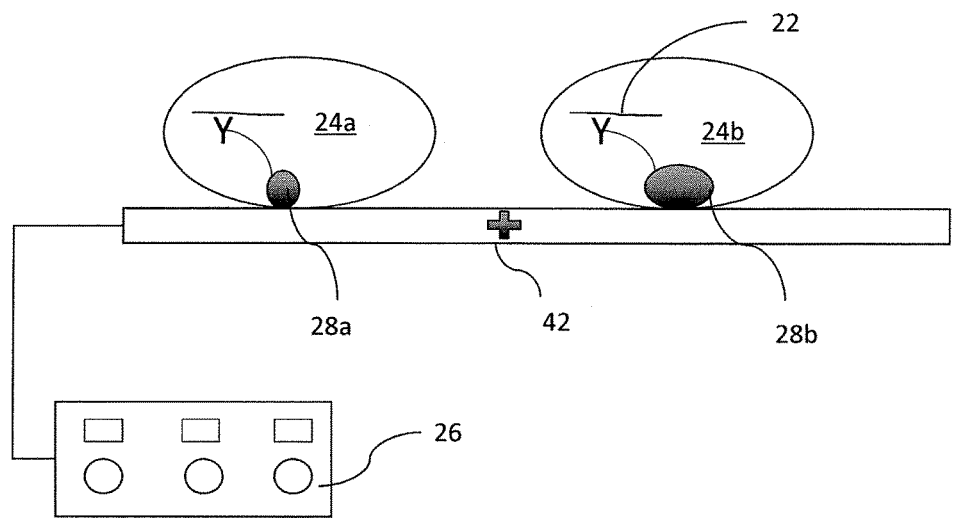

A related approach is shown in FIG. 3B where a binding agent in the form of an antibody 18 specific to an encapsulated biomarker 22 is labeled with a magnetic bead or magnetizable particle 28a, 28b and exposed to an inducible magnetic substrate via the magnetic element 42. Accordingly, binding agents can be labeled with magnetic particles 28a, 28b or particles that are magnetizable and capture of such binding agents can be accomplished by exposing the particles to a suitable magnetic field or a suitable electric field.

Labeling of binding agents with magnetic particles 28a, 28b may be performed using a variety of approaches. In some embodiments, a polypeptide or protein is labeled with a magnetic particle through SH groups on the polypeptide/protein. Other suitable chemistries are available to those skilled in the art and may include the adoption of linkers, chemical modification or the like.

In still further embodiments, the magnetic field, a blocking electric field, dielectrophoretic elements and the like can be selectively activated in response to a signal generated from the presence of exosomes. Such a signal can itself be a detectable change in an electric field or a change in optical property, such as by detecting fluctuations in the electric field due to the presence of exosomes or by detecting binding agents coupled to optically detectable beads, thereby triggering activation. Accordingly, such detectors can include a variety of electrodes coupled to suitable hardware and software to detect changes in impedance, resistance or the like. Alternatively, passage of an exosome through a continuous or modulated light beam may be programmed to trigger and thus activate a variety of electrical elements.

Figure 4:
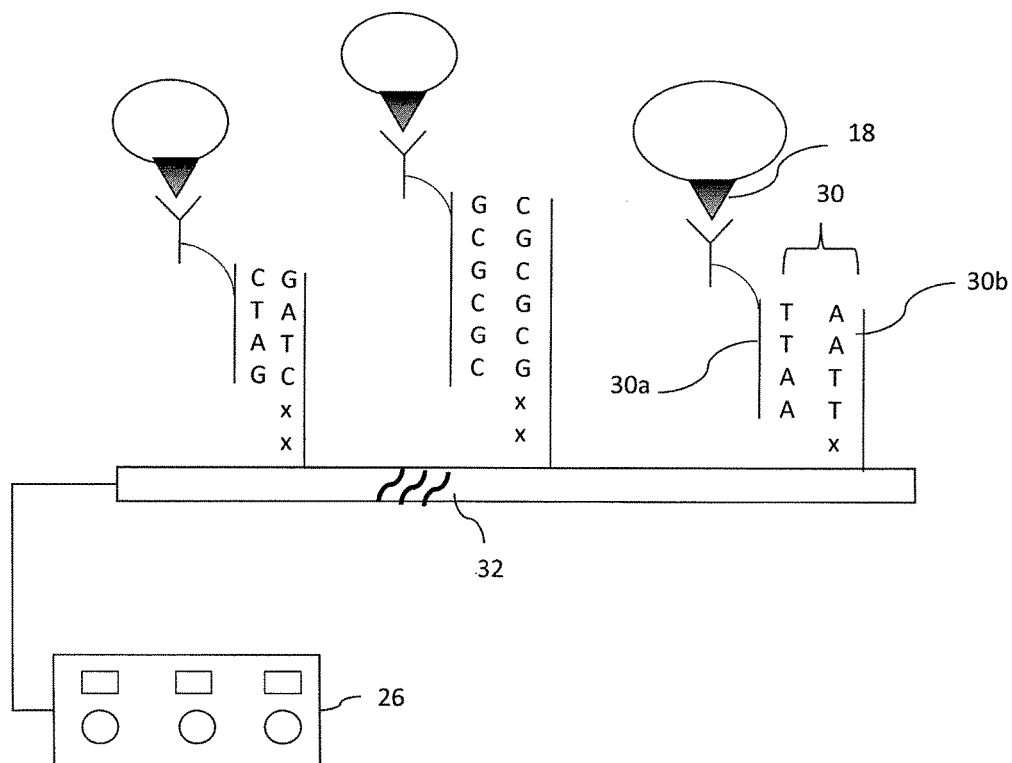

FIG. 4 depicts another variation where instead of permanently immobilizing the binding agent, antibodies 18 are labeled with a single stranded nucleic acid sequence 30a or oligo and permitted to bind to a complementary capture oligonucleotide 30b, itself immobilized to a substrate capable of thermomodulation. This configuration provides an added benefit in that complementary binding between label 30a and immobilized 30b oligos can be modulated by the use of different nucleic acid sequences.

In some instances, labeling antibodies specific to particular subpopulations with different nucleic acid sequences can permit the user to sequentially release the captured exosomes by modulating the temperature of heating element within the substrate, such as by using a base that can modulate the heating element thereby altering resistance to forces from fluid flow or dielectrophoretic forces through the microfluidic device. Such an approach can heat the substrate itself and heat fluid medium in contact with the substrate to modulate the temperature surrounding the nucleic acids. In one embodiment, antibodies for different subpopulations are labeled with nucleic acid sequences having different GC content, thereby exploiting difference in bond strength between G-C as opposed to A-T. In another embodiment, subpopulation specific antibodies are labeled with nucleic acid sequences having a difference in a total number of bases thereby exploiting the differences in strength depending on the length of bonded sequence. In yet another embodiment, antibodies for particular subpopulations incorporate mismatches compared to perfectly complementary sequences. In addition to increasing the temperature of the substrate, release can be accomplished by increased fluid flow rate or by activation of a dielectrophoretic element, which can be configured to push exosomes towards the exit aperture. Accordingly, the binding agents can be labeled with oligonucleotides, optionally where binding agents for different exosome populations are labeled with different oligonucleotides to permit selective capture to complementary oligonucleotides and optionally selective release from the complementary oligonucleotides.

In other embodiments, the binding agents are labeled with an optical marker and the step of capturing the binding agents is performed by optical detection coupled to a cell sorting apparatus, such as those fluorescent activated cell sorting (FACS). Such labels may include Fluorescein isothiocyanate (FITC), R-phycoerythrin (PE), dinoflagellate Glenodinium (PerCP), Allophycocyanin (APC) and the like as known in the flow cytometry arts.

Figure 5:
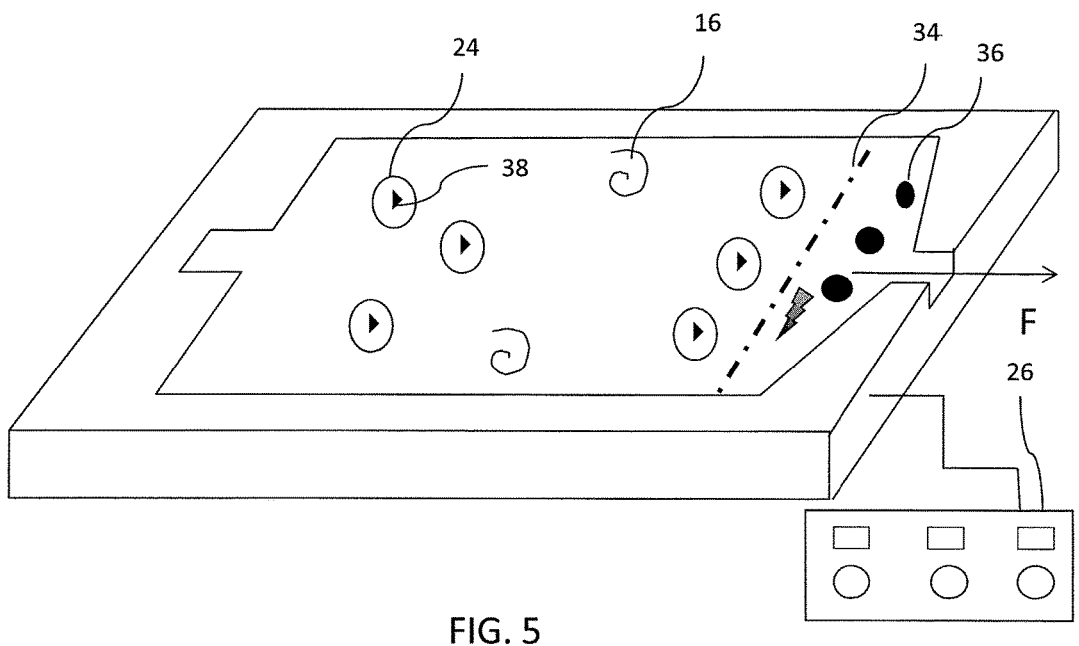
FIG. 5 shows a cutaway view of a microfluidic device, which depicts a flow path F through hollow interior of the capture chamber thereby exposing a sample to dielectrophoretic elements 16 and a blocking electrode element 34.

As shown generally in FIG. 5, in some embodiments the invention provides methods of processing the biological sample, which includes providing a system comprising a microfluidic device, the microfluidic device including a capture chamber having an entry passage and exit passage that are fluidicly coupled, the capture chamber having binding agents 38 that selectively bind subpopulations of exosomes 24 and the capture chamber configured to selectively prevent bound exosomes from exiting the exit passage; providing the mixed exosome population 24, 36 in a liquid medium; and inducing flow of the mixed exosome population 24, 36 through the microfluidic device to capture exosomes 24 bound to the binding agents 38. The binding agents 38 may be external to the exosome 24 or my bind a biomarker within the exosome. The system may also include a device station with a power source 26. In such systems, the capture chamber can include a dielectrophoretic element 16 operable connected to the power source 26, where powering the dielectrophoretic element 16 induces a mixing of the mixed exosome population 24, 36 with binding agents 38 within the capture chamber and/or preventing or diverting the flow of bound exosomes 24 away from the exit passage. Capturing bound exosomes may occur through activation of a blocking electrode 34 that prevents passage of a binding agent-biomarker pair.

In another approach the binding agents are labeled with particles capable of capture by a magnetic field and the capture chamber includes a substrate having an electromagnetic element operably connected to the power source, where powering the electromagnetic element results magnetic attraction between the substrate and the particles thereby preventing flow of bound exosomes from the exit passage of the chamber.

In still another approach the agents are labeled with oligonucleotides and the capture chamber includes a substrate having complementary bound oligonucleotides and that is operably connected to the power source, where powering the substrate results in an increase in temperature thereby permitting release of oligonucleotides from complementary nucleotides.

Figure 6A:
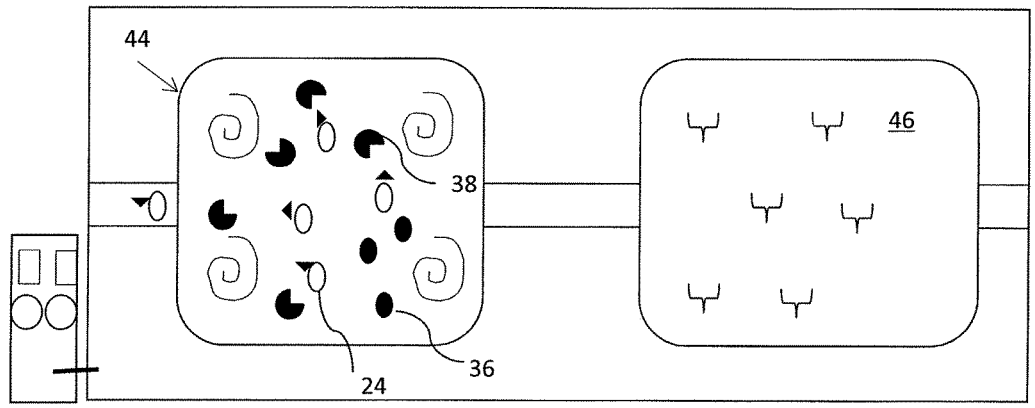
FIGS. 6A-C depict a method of enriching for a subpopulation of exosomes.
Figure 6B:
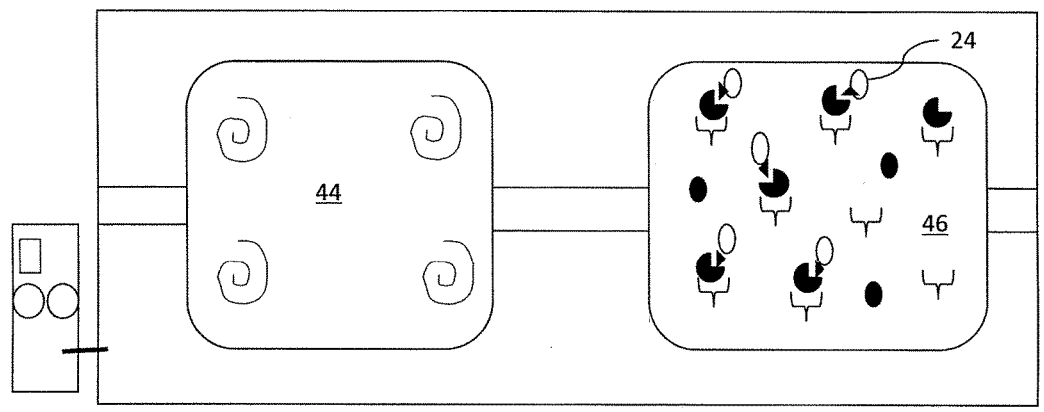
Figure 6C:
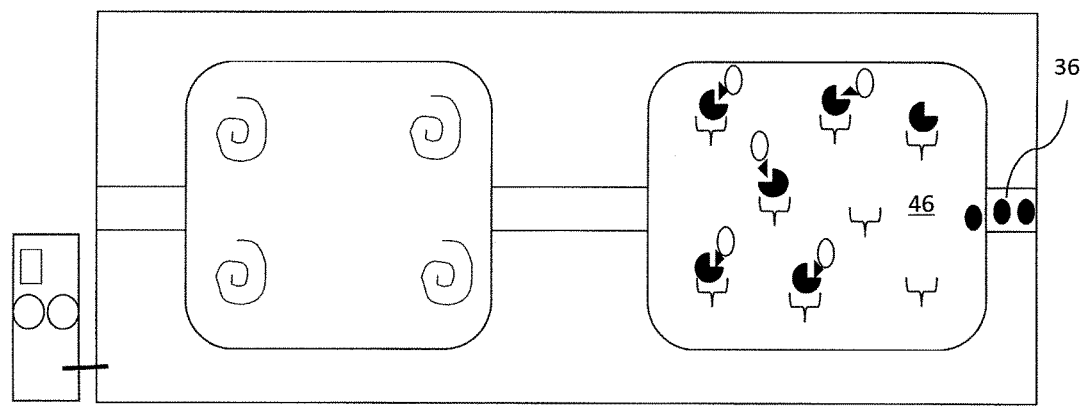

A related approach is depicted generally in FIGS. 6A-6C, where the step of processing the biological sample is performed by providing a system including a microfluidic device having a labeling chamber 44 fluidicly joined and upstream to a capture chamber 46, where the labeling chamber 44 includes binding agents 38 that selectively bind subpopulations of exosomes 24 (FIG. 6A) and the capture chamber 46 being configured to capture exosomes 24 bound to the binding agents 38 and to permit unbound exosomes 36 to pass outward from an exit passage of the capture chamber 46 or device (FIG. 6B); providing the mixed exosome population in a liquid medium; and inducing flow of the mixed exosome population 24, 26 through the microfluidic device to capture exosomes 24 bound to the binding agents 38. As shown in FIG. 6C, unbound exosomes 36 are permitted to flowthrough. In such systems, the capture chamber 46 can be provided with capture molecules, such as immobilized capture molecules, that themselves selectively capture the binding agents 38. This related system can also include a device station 26 having a power source.

In some embodiments, at least one dielectrophoretic element is operably connected to the power source, where powering the dielectrophoretic element results in at least one function such as inducing a mixing of mixed exosome population with binding agents within the labeling chamber, and preventing or diverting the flow of bound exosomes away from the exit passage.

Figure 7A:
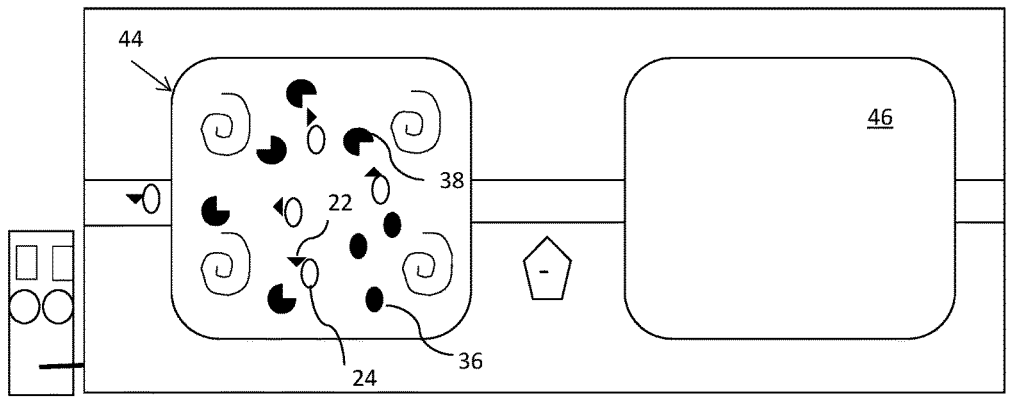
FIGS. 7A-D depict an alternative method of enriching for a subpopulation of exosomes.
Figure 7B:
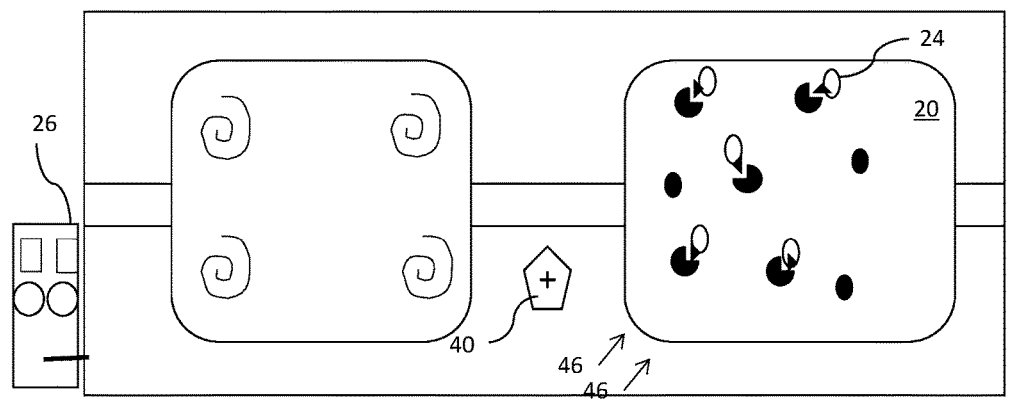
Figure 7C:
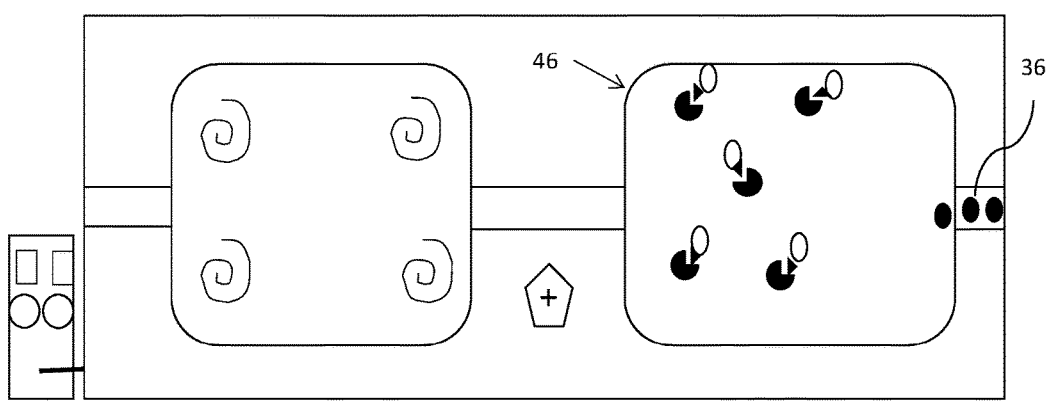
Figure 7D:
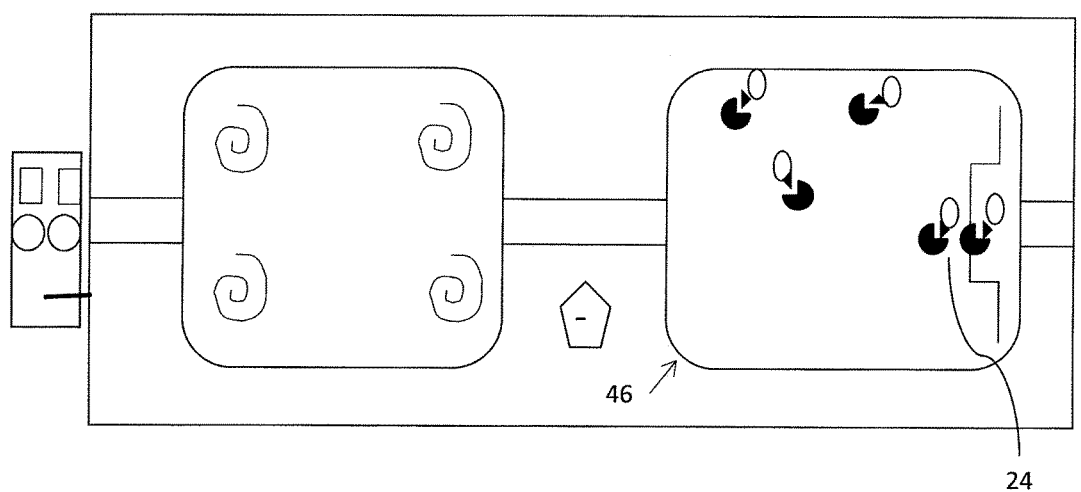

As shown in FIG. 7A, in a related embodiment subpopulations of exosomes 24 are bound to binding agents 38 labeled with magnetic particles in a labeling chamber 44. In FIG. 7B, the capture chamber 46 includes a magnetic substrate 20 operably connected to a power source 26, wherein powering the magnetic substrate 20 selectively captures the bound exosomes 24. In FIG. 7C, exosomes 36 not bound are permitted to exit the chamber 46 for collection. In FIG. 7D, the magnetic substrate 20 is turned off thereby permitting collection of the previously captured exosomes 24.

In another embodiment, the binding agents are labeled with oligonucleotides and the capture chamber includes a substrate having complementary bound oligonucleotides and operably connected to the power source, where powering the substrate results in an increase in temperature thereby regulating capture or release of oligonucleotides from complementary nucleotides.

Figure 8A:
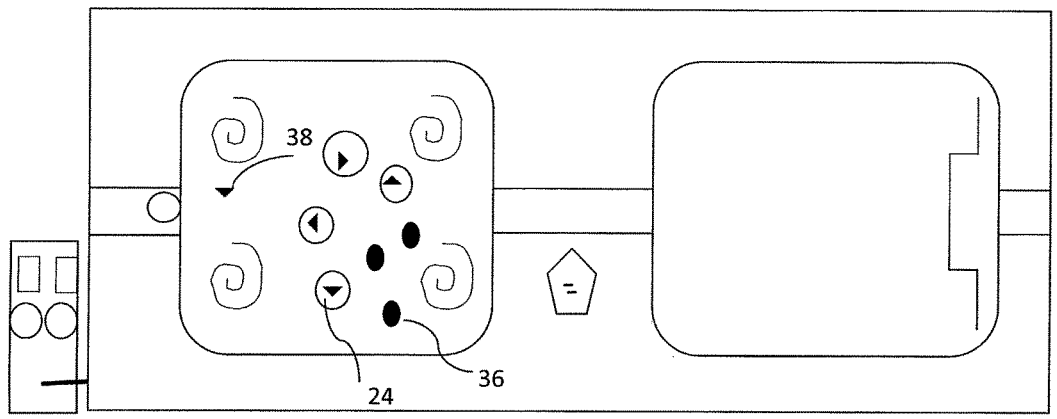
FIGS. 8A-D depict an alternative method of enriching for a subpopulation of exosomes.
Figure 8B:
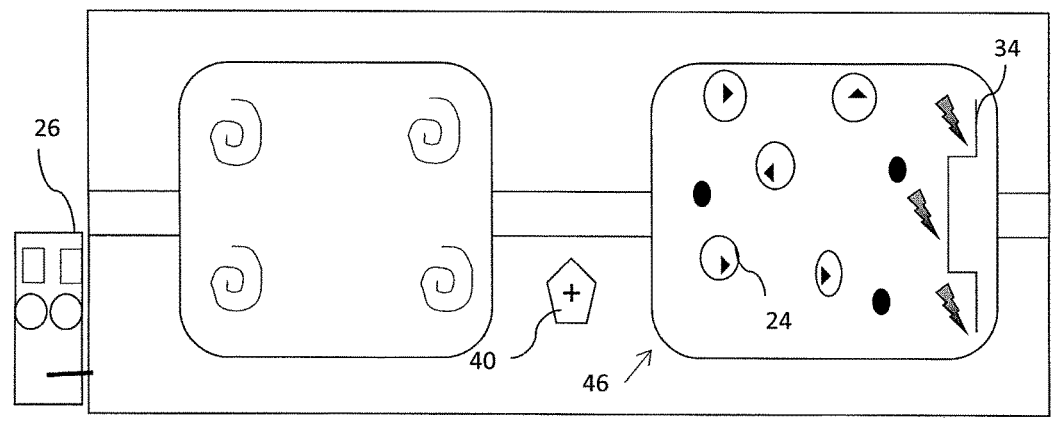
Figure 8C:
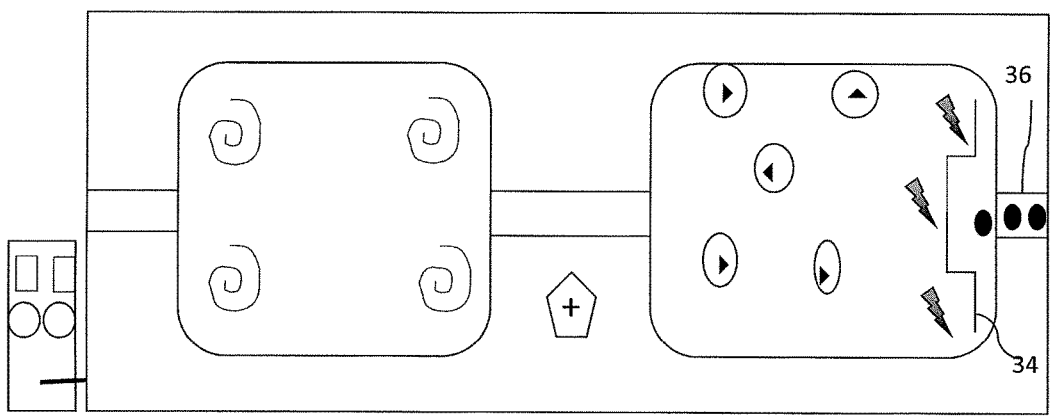
Figure 8D:
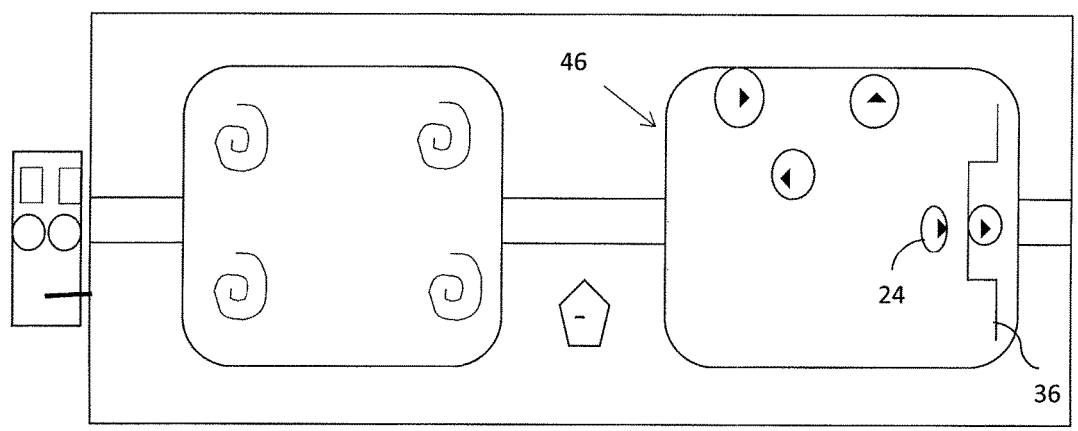

Another variation is shown in FIGS. 8A-8C. In FIG. 8A, exosomes 24, 26 are permeated and biomarkers encapsulated within the exosomes are bound to labeled binding agents 38. In FIG. 8B, the capture chamber 46 includes a blocking electrode 34 operably connected to a power source 26, wherein powering the blocking electrode 34 selectively blocks the bound exosomes 24. In FIG. 8C, exosomes 36 not bound are permitted to exit the chamber 46 for collection. In FIG. 8D, the blocking electrode 34 is turned off thereby permitting collection of the previously captured exosomes 24.

Figure 9A:
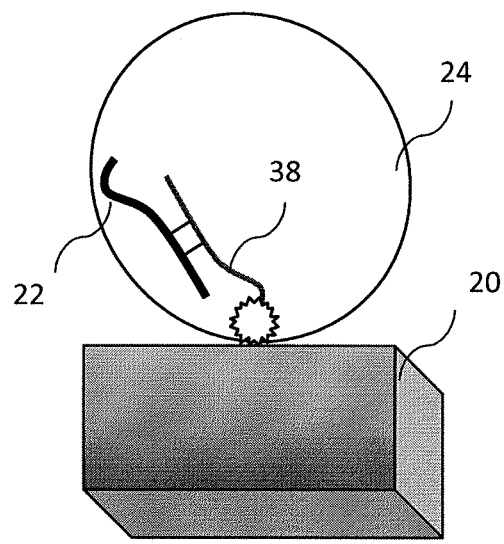
FIGS. 9A-B depict the capture of an exosome 24 using an encapsulated biomarker 22 via a magnetic substrate 20 and the selective release of the exosome 24 from its binding agent through the modulation of temperature while maintaining magnetic attraction to the binding agent 38.
Figure 9B:
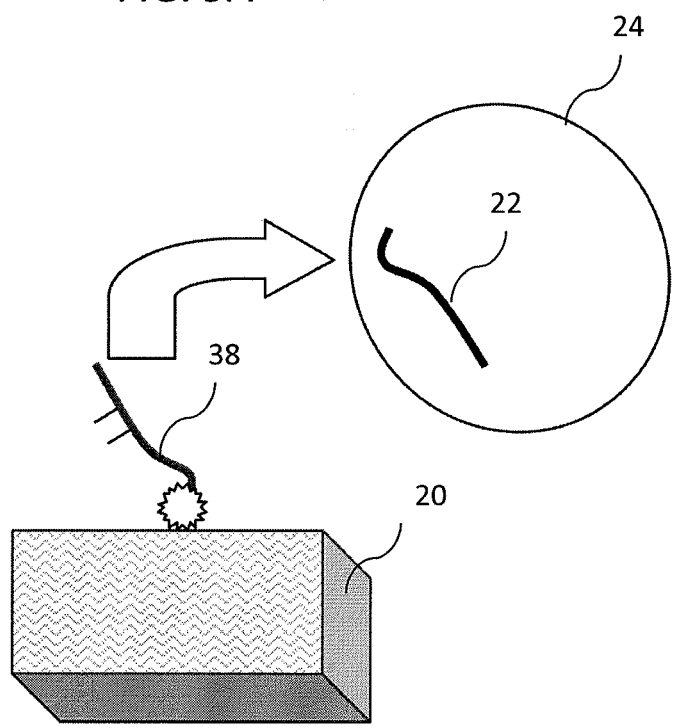

In view of the above, various embodiments involve the selective release of exosome subpopulations such as through modulation of temperature, magnetism, dielectrophoresis and the like. Accordingly, in some instances, it may be desirable to remove the binding agent from the exosome. One such approach is provided in FIGS. 9A-9B. In FIG. 9A an exosome 24 is permeated, thereby permitting binding between an encapsulated biomarker 22 and a magnetically labeled binding agent 38 in the form of a nucleic acid sequence and thus is captured by a magnetic substrate 20. In FIG. 9B, the exosome 24 is released by altering the surrounding temperature to melt the binding agent 38 from the biomarker 22, thereby retaining the binding agent 38 to the magnetic substrate 20 and releasing the exosome 24 with its biomarker 22 for collection.

Figure 10A:
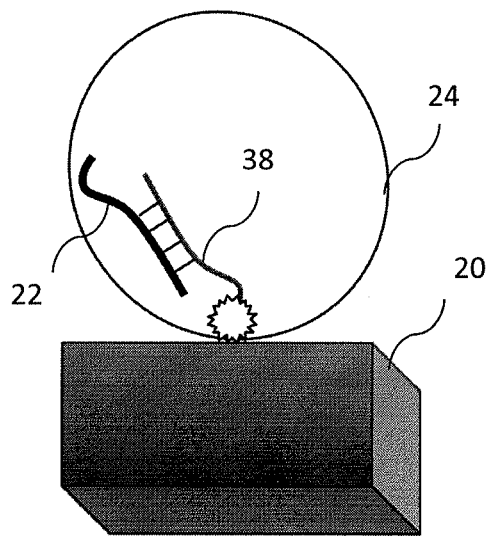
FIGS. 10A-B depict the capture of an exosome 24 using an encapsulated biomarker 22 via a magnetic substrate 20 and the selective release of the exosome 24 from its binding agent 38 under increased temperature compared to that of FIGS. 9A-B.
Figure 10B:
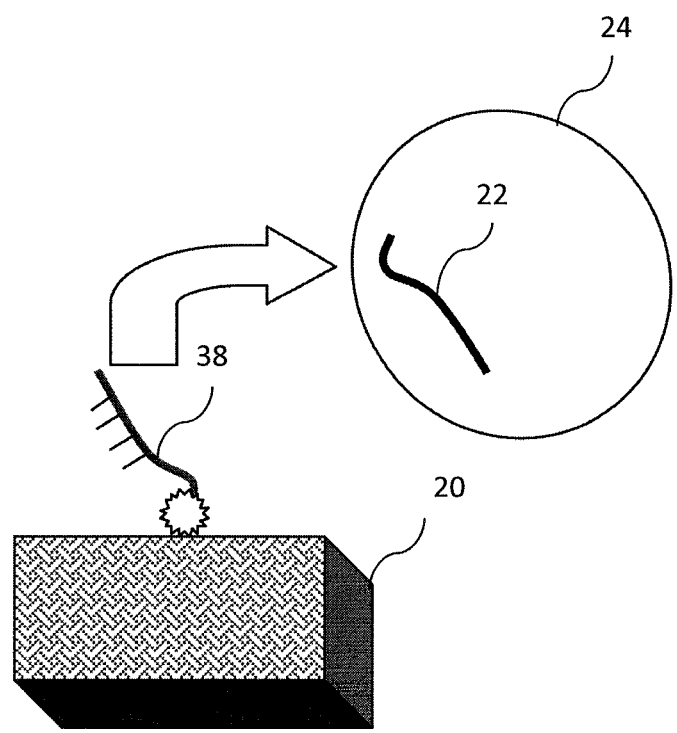

A same approach is provided in FIGS. 10A-10B; however, a binding agent 38 and biomarker 22 for the exosome 24 binds across more nucleic acids and thus would melt later than that of FIGS. 9A-9B, thereby permitting selective release and collection of exosome 24 subpopulations.

Figure 11:
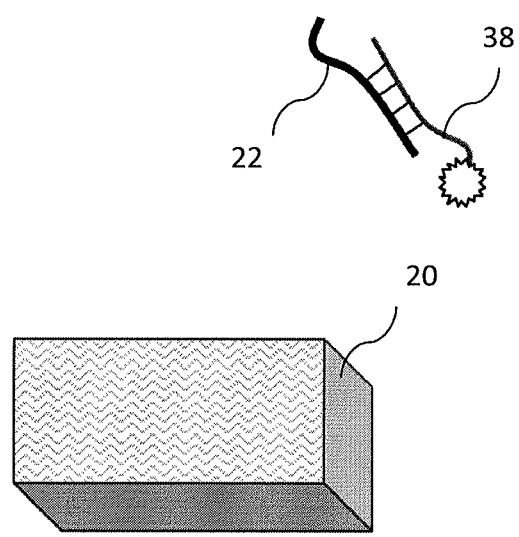
FIG. 11 depicts results after a de-nuding of the binding agent 38—biomarker 22 pair from the surrounding exosome components and its release from the magnetic base 20.

Another approach is demonstrated in FIG. 11, where an exosome 24 is permeated, thereby permitting binding between an encapsulated biomarker 22 and a magnetically labeled binding agent 38 in the form of a nucleic acid sequence and thus is captured by a magnetic substrate 20. The bound exosome is de-nudded, thereby isolating the binding agent 38—biomarker 22 pair from the surrounding exosome 24. The binding agent 38—biomarker 22 pair is then released by deactivating or reversing polarity of the magnetic substrate 20. This example may be followed by performing polymerase chain reaction (PCR) to amplify the biomarker 22. PCR may be performed in the capture chamber or may be performed in another downstream chamber, which includes a appropriate thermocycling substrate.

Figure 12A:
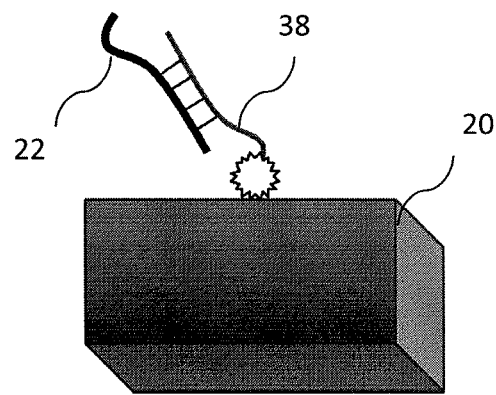
FIGS. 12A-D depict the de-nuding of the binding agent 38—biomarker 22 pair, the release of the biomarker 22 from the binding agent 38, the re-incapsulation of the biomarker 22 into an artificial exosome 48 and the collection of the formed capsule.
Figure 12B:
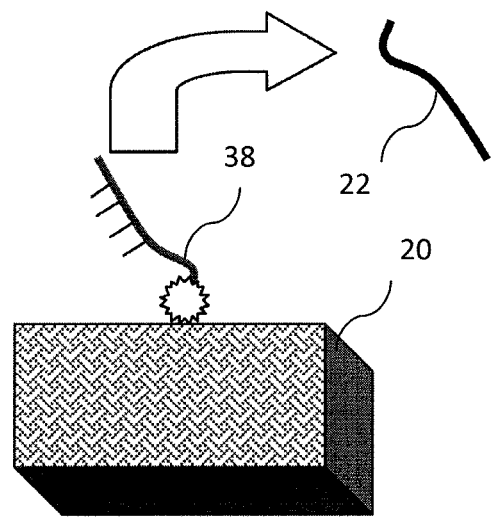
Figure 12C:
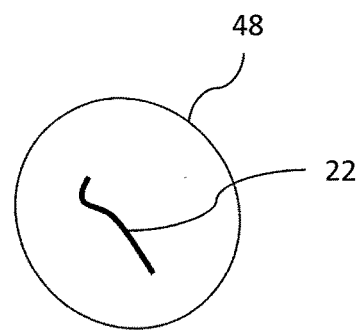
Figure 12D:
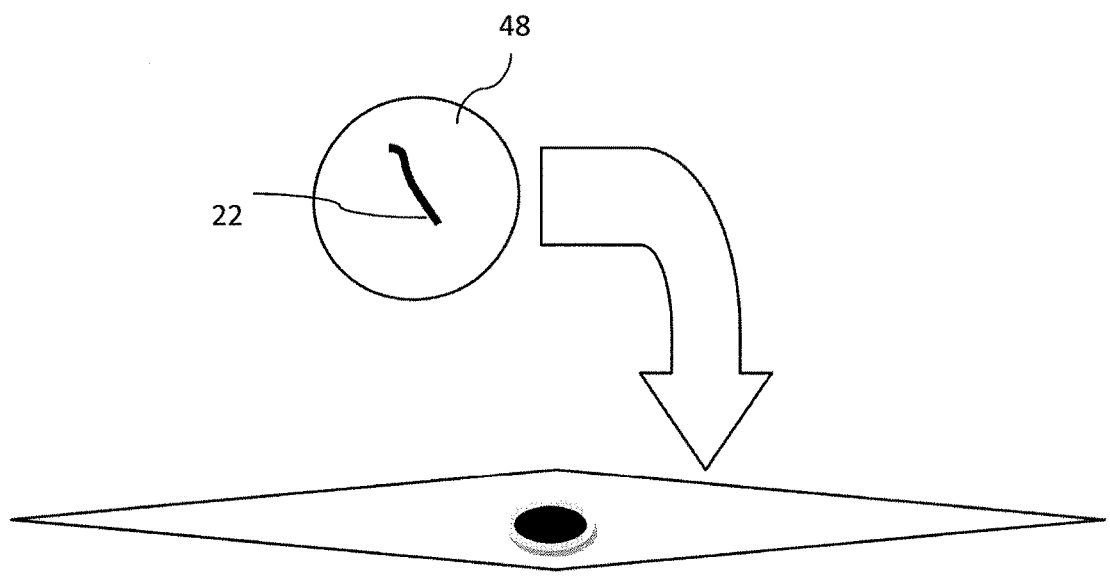

Still another approach is demonstrated in FIGS. 12A-12D. In FIG. 12A, an exosome is permeated, thereby permitting binding between an encapsulated biomarker 22 and a magnetically labeled binding agent 38 in the form of a nucleic acid sequence and thus is captured by a magnetic substrate 20. The bound exosome is de-nudded, thereby isolating the binding agent 38—biomarker 22 pair from the surrounding exosome. In FIG. 12B, the biomarker 22 is released from the binding agent 38 by melting the binding agent 38—biomarker 22 pair (an optionally amplified by PCR) while maintaining magnetic attraction to the binding agent 38. In FIG. 12C, the biomarker 22 is encapsulated in a synthetic exosome 48, and in FIG. 12D the synthetic exosome 48 is captured. This approach may permit the formation of synthetic exosomes 48 with therapeutically beneficial biomarkers 22, while eliminating potential adverse molecules.

As demonstrated to above, in some instances exosomes are permeated or removed from their biomarker. Accordingly, in further embodiments, the method includes approaches to repair or reform exosome vesicles. This may be accomplished at any state where repair or reformation is desired. In some embodiments, exosome vesicle formation is enhanced through exposure to flat plates that are electrically connected, and attached to the power source for current modulation.

Systems for Processing Exosomes

With brief reference to the drawings generally, another aspect of the invention provides a system for processing an exosomes from a biological sample having a mixed population of exosomes, the system including a microfluidic device, the microfluidic device itself including a capture chamber 46 having an entry passage 12 and exit 14 passage that are fluidicly coupled, the capture chamber 46 having binding agents 38 that selectively bind subpopulations of exosomes 24 and configured to selectively prevent bound exosomes 24 from exiting the exit 14 passage. In some embodiments, the binding agents 38 are immobilized to a substrate 20. In some embodiments, the capture chamber 46 permits the capture then release or selective release of bound exosomes 24.

In a related aspect, the invention also provides a system for processing exosomes from a biological sample having a mixed population of exosomes, the system including a microfluidic device having a labeling chamber 44 fluidicly joined and upstream to a capture chamber 46, wherein the labeling chamber 44 has binding agents 38 that selectively bind subpopulations of exosomes 24 and the capture chamber 46 being configured to capture exosomes 24 bound to the binding agents 38 and to permit unbound exosomes 24 to pass outward from an exit 14 passage. In further embodiments, the capture chamber 46 permits the release or selective release of bound exosomes 24.

In some embodiments, fabricating a suitable microfluidic device can be accomplished by providing a substrate, and laser ablating the substrate to form suitable channels, wells or contours. Elements, such as delectrophoretic elements, magnetic elements, heating elements, electric plates, electrode barriers or the like can be inserted into laser ablated recesses, adhesively attached to the substrate, or the like. Alternatively, or in addition, a substrate may be formed with suitable channels and contours using injection molding of materials such as polymer plastic. In some embodiments, an electrically conductive material is adhesively fixed to the substrate, followed by laser ablation to form electrodes.

Immobilizing binding agents or capture agents to the substrate can be performed using bonding layers, polymer coatings, chemical conjugation to a functionalized substrate surface, such as by treatment with plasma or the like as known in the microfluidic arts.

A top layer may be fused or bonded to the substrate to form the hollow chamber. The skilled artisan will appreciate that either the upper or lower portion may be drilled or laser ablated to form entry or exit ports as known in the microfluidic arts. Further, a transparent top or bottom may be preferred in instances where optical detection in either chamber is desired.

Naturally, electronic devices such as dielctrophoretic elements, electromagnets, electrode barriers, optical detectors, heating elements or the like can be configured for electrical connection to an external power source or device station and thus may include electrical leads or traces leading to a portion of the microfluidic device that is connectable to a power source. Accordingly, the device may incorporate edge connectors, clips, switches or the like as known in the electrical arts.

When providing binding agents that are not immobilized, the binding agents may be lyophilized into a lyophilized ball and stored in either a labeling or capture chamber. Alternatively, binding agents may be added to the labeling chamber (or capture chamber) through the entry aperture during use or be provided in an adjacently coupled reagent reservoir.

Formulations for Medical Treatment or use in Research

Exosomes can be further processed by combining one or more desired subpopulation of exosmes with a pharmaceutically acceptable carrier to form a pharmaceutical. Similarly, one or more desired subpopulation of exosomes can be combined with a cosmetically suitable carrier to form a cosmetic. Thus, the invention also provides a method of introducing one or more desired exosome subpopulations to a subject, which includes processing a subpopulation from a biological sample, forming a pharmaceutical and introducing the pharmaceutical to the subject. Similarly, the invention also provides a method of introducing one or more desired exosome subpopulation to a subject, which includes processing a subpopulation of exosomes from a biologic sample, forming a cosmetic and introducing the cosmetic to the subject.

In some embodiments, the desired exosome subpopulation is used for autologous therapeutic treatment in the original subject in the form of a skin cream, a skin lotion, a skin gel, a skin powder, a skin spray, a skin sol-gel, an oral pill, an oral syrup, an intravenous solution, an intradermal solution, a tissue injection or the like.

The pharmaceutical or cosmetic formulations may be used to treat a variety of conditions alone or in combination with other treatments. For example, the compositions may be use for skin rejuvenation, anti-ageing, scar remodeling, wound healing, wrinkle reduction, acne therapy and limb salvage.

One skilled in the present at will realize that formulations for pharmaceuticals or cosmetics can vary depending on the route of administration. As such, the desired exosonies may be combined with suitable pharmaceutically acceptable excipients, carriers, or diluents. In formulations, surfactants, diluents, sweeteners, disintegrants, binders, lubricants, glidants, colorants, flavors and mixtures thereof can be used.

Diluents may include, but are not limited to, mannitol, sorbitol, xyfltol, microcrystalline cellulose, silicified microcrystalline cellulose, hydroxypropyl methylcellulose, hydroxypropyl cellulose, pullulan and fast dissolving carbohydrates such as Pharmaburst™, mixtures thereof and the like.

Glidants may include, but are not limited to, silicon dioxide, colloidal silicon dioxide, calcium silicate, magnesium silicate magnesium trisilicate, talc, starch, mixtures thereof and the like.

Binders may include, but are not limited to, sodium alginate, cellulose, methylcellulose, ethyl-cellulose, hydroxypropyl cellulose, hydroxypropyl methylcellulose, sodium carboxymethyl cellulose, polypropylpyrrolidone, polyvinylprrolidone, gelatin, polyethylene glycol, starch, pre-gelatinized starch, sugars, trehalose, glucose, tragacanth, sorbitol, acacia, alginates, carrageenan, xanthan gum, locust bean gum and gum arabic, waxes, poly acrylamide, mixtures thereof, and the like.

Lubricants may include, but not limited to, calcium stearate, glyceryl monostearate, glyceryl behenate, glyceryl palmitostearate, hydrogenated vegetable oil, light mineral oil, magnesium stearate, mineral oil, polyethylene glycol, poloxamer, sodium benzoate, sodium lauryl sulfate, sodium stearyl fumarate, stearic acid, talc, zinc stearate, mixtures thereof and the like.

Disintegrants may include, but are not limited to, sodium starch glycolate, sodium carboxymethyl cellulose, calcium carboxymethyl cellulose, croscannellose sodium, crospovidone, alginic acid, chitosan, methyl cellulose, microcrystalline cellulose, powdered cellulose, lower alkyl substituted hydroxypropyl cellulose, polactilin potassium, starch, pregelatinized starch, sodium alginate, mixtures thereof or whatsoever.

In addition to the use of subpopulations in pharmaceuticals or cosmetics, desired subpopulations may be used in culture to affect harvested or cultured cell populations prior to reintroduction into the subject.

In other embodiments, formulations including the desired exosomes are for purposes of lipolysis and/or microbicidal activity and/or induction of cell death and/or apoptosis. In still other embodiments formulations incorporating exosomes are used for diagnostic or research purposes.

In view of the above, the skilled artisan will appreciate that the desired exosomes can be used in an allogeneic or xenogenic fashion.

EXAMPLES

Example 1

Processing a Total Exosome Population into Distinct Subpopulations

A microfluidic device utilizing a magnetic capture approach as set forth above is provided for a processing method. A population of total exosomes harvested from serum of a subject is added to the microfluidic device. The total exosome population is permeated and mixed with binding agents labeled with magnetic particles in a labeling chamber, the binding agents being oligonucleotides of different length or sequence for each target exosome subpopulation. The sample is then transferred to the capture chamber where a magnetic substrate is induced to capture exosomes bound to the binding agents. Unbound exosomes are permitted to flow out of the capture chamber. While maintaining the magnetic field, the temperature of a heating element is raised stepwise to selectively release bound exosomes by subpopulation and provided for collection.

Example 2

Processing a Total Exosome Population into Distinct Subpopulations

A microfluidic device utilizing a magnetic capture approach as set forth above is provided. Blood is collected from a subject and a total exosome population is collected from the serum. The total exosome population is added to the microfluidic device. The total exosome population is permeated and mixed with binding agents labeled with magnetic particles in a labeling chamber, the binding agents being oligonucleotides of different length or sequence for each target exosome subpopulation. The sample is then transferred to the capture chamber where a magnetic substrate is induced to capture exosomes bound to the binding agents. Unbound exosomes are permitted to flow out of the capture chamber and are collected.

Subpopulations of bound exosomes are then selectively released by heating the capture chamber to release the binding agents from the biomarkers. The exosome is then heated to dissociate the native sense strand and nascent antisense strand and new probe-labels are introduced to allow capture of the sense strand. This is done by allowing the sense label-probe to anneal, but then quickly quench the reaction to a low temperature essentially creating a single stranded conformations between the sense and antisense strands. The capture element is then turned on to essentially remove the native sense strand. In this way a "switch out" of sense for antisense occurs within the exosome. The new exosomes are then washed free from the chamber for collection. This process may be repeated several times prior to final wash-out of exosomes to either selectively create antisense copies to the original existing nucleic acid exosome within the naturally occurring exosome or may be used to selectively create sense copies of the exosome and further processed to package or create new exosomes using appropriately modified label-probes and subsequent processing of the exosomes (such as capacitor plate or electrical plate vesicle formation).

What is claimed is:

1. A method of processing exosomes from a biologic sample, comprising:
   a) providing a biological sample having a mixed population of exosomes comprising two or more subpopulations of exosomes having a different subpopulation characteristic;
   b) labelling a subpopulation of exosomes by binding RNA molecules encapsulated within the subpopulation to labelled binding agents;
   c) selectively capturing the labelled subpopulation of exosomes to remove the labelled subpopulation from the mixed population of exosomes thereby obtaining a sample enriched with a desired subpopulation of exosomes; and
   d) adding the enriched sample of exosomes to a pharmaceutically acceptable carrier.

2. The method according to claim 1, wherein the step of selectively capturing the labelled binding agents permits passage of remaining exosomes.

3. The method according to claim 1, wherein the label is a magnetic particle or a particle that is magnetizable and the step of capturing the labelled subpopulation comprises exposing particles to a magnetic field or an electric field.

4. The method according to claim 3, wherein the particles have different characteristics that permit capture and selective release by modulation of the magnetic field or the electric field.

5. The method according to claim 3, wherein the binding agents are oligonucleotides labeled with magnetic particles for capture using a magnetic field.

6. The method according to claim 5, further comprising de-nuding a binding agent and RNA molecule pair from the surrounding exosome.

7. The method according to claim 1, wherein the enriched subpopulation is a captured subpopulation.

8. The method according to claim 1, wherein the enriched subpopulation is a subpopulation that is not captured.

9. The method according to claim 1, wherein the step of labelling the subpopulation of exosomes comprises permeating exosome membranes to accept a binding agent prior to capture.

* * * * *